United States Patent [19]

Fraenkel et al.

[11] Patent Number: 4,962,255

[45] Date of Patent: * Oct. 9, 1990

[54] CATALYSTS AND PROCESS FOR THE PRODUCTION OF HYDROCARBONS AND SUBSTITUTION OF HYDROCARBONS

[75] Inventors: Dan Fraenkel; Moshe Levy; Baruch Ittah, all of Rehovot, Israel; Margaret Cherniavsky, late of Rehovot, Israel, William Cherniavsky, executor

[73] Assignee: Yeda Research & Development Company Limited, Rehovot, Israel

[ * ] Notice: The portion of the term of this patent subsequent to Jun. 3, 2003 has been disclaimed.

[21] Appl. No.: 319,865

[22] Filed: Mar. 6, 1989

Related U.S. Application Data

[63] Continuation of Ser. No. 783,011, Oct. 2, 1985, abandoned.

[30] Foreign Application Priority Data

Oct. 2, 1984 [IL] Israel ......................................... 73146

[51] Int. Cl.$^5$ ................................................. C07C 2/66
[52] U.S. Cl. ...................................... 585/467; 585/468
[58] Field of Search ................................ 585/467, 468

[56] References Cited

U.S. PATENT DOCUMENTS

| 4,016,218 | 4/1977 | Haag | 585/467 |
| 4,187,255 | 2/1980 | Dodd | 585/467 |
| 4,469,908 | 9/1984 | Burress | 585/467 |
| 4,593,137 | 6/1986 | Frenckel | 585/467 |

FOREIGN PATENT DOCUMENTS

| 0126245 | 11/1984 | European Pat. Off. | 585/467 |
| 3334084 | 4/1985 | Fed. Rep. of Germany | 585/467 |
| 0954382 | 8/1982 | U.S.S.R. | 585/467 |

Primary Examiner—Asok Pal
Attorney, Agent, or Firm—Browdy and Neimark

[57] ABSTRACT

A method of selective beta-alkylation of aromatic substrates such as naphthalene or a derivative thereof, comprising reacting the substrate with an alcohol or olefin alkylating agent in the presence of a catalyst selected from the group consisting of a crystallized borosilicate glass zeolite and a crystalline alumina-silica catalyst, said catalyst being at least 86% beta selective with respect to the alkylation of naphthalene by the alkylating agent.

7 Claims, No Drawings

CATALYSTS AND PROCESS FOR THE PRODUCTION OF HYDROCARBONS AND SUBSTITUTION OF HYDROCARBONS

This application is a continuation, of application Ser. No. 06/783,011, filed on Oct. 2, 1985, now abandoned.

FIELD OF THE INVENTION

The invention relates to novel crystallized borosilicate glass zeolite catalysts and to a process for the production of these. The invention further relates to a process for the conversion of lower alkanols, preferably methanol, to gasoline like hydrocarbon mixtures. The invention further relates to the use of such catalysts, and of crystalline silica-alumina catalysts for the beta-selective alkylation of naphthalenes, yielding mixtures of 2-alkyl, and 2,6-as well as 2,7-dialkyl napthalene.

DESCRIPTION OF PRIOR ART

Molecular sieve aluminosilicates, known as zeolites, are effective catalysts in a variety of hydrocarbon conversion reactions. Several types of molecular sieves characterized by a high silica-to-alumina ratio (Si:Al$\geq$5), such as zeolite Y and mordenite in their acidic form are effective catalysts in aromatic hydrocarbon alkylation. For example, zeolite catalyzed toluene alkylation is present in U.S. Pat. Nos. 3,965,208; 4,100,215; 4,127,616; Yashima et al., J. Catalysis, 16, 273 (1970); E. Biron, Ph.D Thesis, 1975, The Weizmann Inst. of Sci.

Due to the pore structure of zeolites which is made of uniform channels characterized by effective openings ranging between ca. 5 and ca. 10 Å, zeolite catalysts possess shape-selective properties. In the alkylation of toluene, for instance, where ortho, meta and para alkyltoluene isomers are produced, there is strong preference in some modified zeolites for the formation of the para isomer since this isomer has the smallest cross-sectional diameter enabling it to diffuse more easlity through the zeolite channels, as compared with the other isomers.

Recently, high-siliceous pentasil zeolites with effective pore diameters in the 5–6 Å range have been synthesized by Mobil Oil Corp. e.g., U.S. Pat. No. 3,702,886 describing the preparation of ZSM5. These aluminosilicates in their acidic form show dramatic catalytic activity with exceptionally high thermal stability and aging resistability in the methylation (e.g. Kaeding et al., J. Catalysis, 67, 159 (1981); Brit. No. 1,574,523; U.S. Pat. Nos. 3,965,207; 4,250,345; 4,034,053), ethylation (e.g., U.S. Pat. Nos. 4,143,084; 4,117,024) and transalkylation (disproportionation) (e.g., Kaeding et al., J. Catalysis, 69, 392 (1981); U.S. Pat. No. 4,067,920) of toluene, and in the conversion of methanol to aromatics - rich hydrocarbon mixtures (e.g., U.S. Pat. Nos. 4,138,440, 3,894,107).

Prior art on the catalytic gas phase alkylation of naphthalene with methanol does not show substantial beta-selectivity in the alkylnaphthalenics obtained. For example, Conoco Company (J. R. Dodd, U.S. Pat. No. 4,187,255) has disclosed the alkylation of naphthalene with methanol at 450°–600° C. and 400 psi over alumina catalysts (such as CATAPAL®), giving a beta-to-alpha methylnaphthalene ratio of <4. Another example (H. H. Tso et al., Bull. Inst. Chem., Acad. Sin. 28, 71-4 (1981) describes the alkylation of naphthalene with methanol at 450° C. over Nikki N631-L silica-alumina catalyst affording a beta-to-alpha ratio of $\approx$2.5.

In contrast to the prior art as described heretofore, novel aluminosilicate catalysts are prepared by crystallizing boroaluminosilicate glasses of the type sold as PYREX, in the presence of a template such as tetraalkylammonium hydroxide; these catalysts are highly shape-selective in acid catalyzed reactions such as the conversion of methanol to $C_5$–$C_{11}$ hydrocarbon mixtures and, in particular, highly beta-selective in the alkylation of naphthalene. Beta-selectivity exceeding 90% (i.e., a beta-to-alpha methylnaphthalene ratio of >8) is typical. Previous zeolite preparations from glasses, e.g., U.S. Pat. Nos. 3,714,366 (Fukuda et al.) 4,211,756 (Johnson), Can. No. 1,142,905 (Marosi), French No. 1,584,496 (Bayer), and others, do not disclose the reaction of PYREX glass with the presently disclosed templates to afford a highly efficient catalyst for methanol conversion or a highly beta-selective catalyst for the alkylation of naphthalene.

The conversion of methanol to $C_5$–$C_{11}$ mixtures rich in aromatics is an important potential route for synthetic gasoline, since any carbonaceous resource, e.g., coal, natural gas, etc., can be a raw material in the production of methanol through the intermediate formation of synthesis gas ($CO+H_2$).

Methylnaphthalenes are important materials in industry. Beta-methylnaphthalene can be oxidized to vitamin $K_3$ (menadione), whereas alph-methylnaphthalene is useful as a fuel additive, a plasticizer in PVC, an intermediate for preparing rubber additives and an intermediate in the preparation of fungicides. 2,6-dimethylnaphthalene, which, in the process disclosed in this embodiment can be obtained in situ selectively by beta-methylation of beta-methylnaphthalene, is used for the commercial production of the corresponding diacid from which polyester films and fibers of superior properties, as compared to the conventional materials based on terephthalic acid are manufactured.

SUMMARY OF THE INVENTION

The present invention provides crystallized glass zeolite catalysts for the selective production of gasoline-like mixtures from methanol and beta-position alkylation of naphthalene compounds.

There is also provided a process for preparing selective crystallized glass zeolite catalysts for the conversion of methanol to gasoline-like product and beta-selective alkylation of naphthalene type compounds with $C_1$–$C_3$-alkanols or olefins, which comprises reacting a source of PYREX with a suitable template at elevated temperatures. Si and Al from non-PYREX sources may be added to the reaction system, if desired.

There is also provided a process of preferred production of gasoline-like mixtures from methanol and preferred beta-position alkylation or naphthalene and derivatives thereof, which comprises reacting methanol, or the substrate with alkylation agent while passing methanol, or the substrate and alkylation agent through a catalyst-loaded column at an elevated temperature. Preferred substrates are naphthalene and beta-methylnaphthalene, and preferred alkylation agents are $C_1$–$C_3$-alkanols.

DETAILED DESCRIPTION OF THE INVENTION

According to the invention, crystallized glass zeolite catalysts are prepared by reacting a fine powder of borosilicate glass with a template of the type conventionally employed in the synthesis of ZSM5 catalysts.

Borosilicate glasses having a boric oxide content of up to about 15% and a thermal expansion coefficient of less than about 40 ($\times 10^{-7}/°$ C.) are preferred.

Suitable borosilicate glasses broadly comprise the low-expansion commercial borosilicate glasses generally available under the trademark PYREX, such as PYREX Glass Codes 7720, 7740 and 7760, manufactured by Corning Glass Works, Corning, N.Y., or Sovirel Glass such as 732.01 These are preferably used as fine powders. Powders of 80–100 mesh (Tyler) and smaller are very suitable. The preferred powders are of >200 mesh and the most preferred of 400–500 mesh. Templates useful in the process of the present invention broadly include tetraalkylammonium hydroxides such as tetra-propylammonium hydroxide (TPAH) and tetra-ethylammonium hydroxide (TEAH), or the corresponding chlorides, bromides, or iodides. Other compounds such as 1,6-hexanediol or 1,6-hexanediamine (hexamethylenediamine) also function as templates. The templates may also be prepared in situ, e.g., from a starting mixture containing the corresponding trialkylamine, plus alkyl halide. The most effective reaction system comprises PYREX powder in combination with TPAH, with or without added Si or Al from non-PYREX sources; the system is conventionally reacted in an autoclave lined with TEFLON or other inert materials.

According to the invention, the PYREX-template system is reacted at an initial nucleation pH of $\geq 13$ at temperature of from about 100° to 200° C. for a period of time of at least 1 hour, and up to about 7 days. Larger PYREX particles will generally require more time than powders to effect the reaction; and give poor catalyst material; temperatures of from about 160° C. to about 200° C. for from about 1 to 3 days, will generally suffice, with temperature of about 190° C.± for 1 day being usual. Broadly, a ratio (w/w) of about 1:1 to 2:1 PYREX to TPAH or other template, and preferably about 1.5:1, will give the desired product.

As previously noted, the crystallized glass zeolite of the invention may be modified during production by addition of, e.g. Si or Al from non-Pyrex sources.

Generally, the zeolites of the invention are finished by drying and heating to 540° C. to evacuate the microcrystalline pores and channels from water and TPAH molecules, and calcining the remaining aluminosilicate product. The range of temperatures for effective decomposition of TPAH and calcining is 450°–650° C. The preferred range is 500°–600° C. To become catalytically active in alkylation, the calcined zeolite has to be converted to its hydrogen form, e.g., via its ammonium form.

Ammonium ion exchange can be performed using a solution of ammonium ion such as salts, preferably ammonium chloride, nitrate or sulfate. The hydrogen form of the zeolite is then obtained by heating to a desired temperature in the range of 450°–550° C. for a period typically in the range of 0.5–10 hours, commonly between 1 and 3 hours, to decompose the ammonium ion according to the equation.

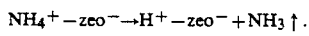

$NH_4^+ - zeo^- \rightarrow H^+ - zeo^- + NH_3 \uparrow$.

Instead of this indirect proton exchange, a direct exchange can be performed using acids, particularly inorganic acids, such as hydrochloric acids, nitro acid, sulfuric acid or others in dilute solutions.

EXAMPLE 1

6.2 g $SiO_2$ (Davison grade 950) was dissolved in 67.5 g of TPAH solution (20% in water, Fluka 88110) by gentle heating. The solution was evaporated to a final weight of 50 g. To this was added dropwise, under stirring, 1.35 g of a solution of sodium aluminate prepared by dissolving 1.0 g aluminum (turnings), in a solution of 1.8 g NaOH (pellets, analytical, Merck) in 5.0 g $H_2O$, and evaporating to a final weight of 7.0 g. A gel was formed instantly and it was allowed to equilibrate with the solution for about 1 h. The obtained mixture was transferred into a Teflon-lined autoclave, which was closed, heated to 152° C. and kept at this temperature for 5 days. Then the autoclave was cooled and opened and its content was poured into a filtration funnel. After filtration, repeated washing with deionized water, drying overnight at 120° C. and, finally, calcination at 540° C. for 3 h, 6 g solid was obtained. This solid was ion-exchanged twice with 75 ml 1N $NH_4Cl$ solution for 2 h at ambient temperature to afford, after washing and drying at 120° C. overnight 5.5 g of a colorless powder. XRD spectrum of the solid shows that the aluminosilicate obtained has a structure typical to ZSM5-like zeolites.

EXAMPLE 2

This Example describes the effectivity of the solid obtained in Example 1 as a beta-selective catalyst in the alkylation of naphthalene with methanol. 0.5 g of the solid catalyst mixed with 2.5 g glass bead was loaded between glass-wool stuffing in a 20 mm I. D. PYREX tubular reactor surrounded by electrical heater equipped with a thermoregulator. This catalyst mixture was first preactivated at 300° C. for 2 h under flow of air, 60 cc/min then at 450° C. for 0.3 h under Ar, 60 cc/min. Then, the temperature was reduced to 400° C. and, while the argon stream continued at the same rate, a feed of mesitylene:naphthalene;methanol (molar ratio, 3.57:1.00:6.61 respectively) was added from a Sage syringe pump model 341, placed on top of the reactor, at a rate of 2.1 ml per hour. Samples were taken periodically from the bottom exit of a water-cooled condenser placed below the reactor. The samples were analyzed gas chromatographically using a 30 m SP-2100 capillary column, a 30 m SE-$\overset{3}{\nu}$ capillary column, and a 4 m SE-30 column. Results are summarized in Table 1.

The results in Table 1 show that the solid obtained in Example 1 is an efficient and beta-selective catalyst for the alkylation of naphthalene with methanol. Under the above conditions which are given only as illustration and by no means restricts the scope of the present invention, this catalyst is far better in beta-selectivity, albeit less reactive than H-Mordenite (Zeolon 200-H, from Norton Company) and HY (which is a calcined $NH_4$-Y obtained by ion exchanging SK-40 zeolite from Union Carbide with a $NH_4Cl$ solution). Also, the catalyst of Example 1 gives higher yields of methylnaphthalene and dimethylnaphthalene and depresses polyalkylation products.

EXAMPLE 3

A solid aluminosilicate catalyst was obtained as in Example 1 but starting with 6.2 g $SiO_2$ and 13.6 g TPAH.

EXAMPLE 4

A solid boroaluminosilicate catalyst was obtained as in Example 1, but starting with 6.2 g $SiO_2$, 0.64 g $B_2O_3$ and 13.6 g TPAH.

EXAMPLE 5

A solid boroaluminosilicate catalyst was obtained as in Example 1, but starting wiht 15 g PYREX glass (>200 mesh) and 50 g TPAH. The synthesis took place at 195° C. for 7 days.

EXAMPLE 6

A solid boroaluminosilicate catalyst was obtained as in Example 5 but with one-third of a synthesis mixture and a time of 1 day.

Table 2 summarizes results obtained with the catalysts of Examples 3–6, as compared with those of H-Mordenite (HM), using the procedure and analytic method described in Example 2. The temperature of the catalytic runs was 500° C. and the carrier gas (Ar) flow rate, ~20 ml/min. As seen, the obtained catalysts (Examples 3–6) are more efficient than HM at 500° C. in producing beta-alkylation naphthalenic products. The beta-to-alpha ration in methylnaphthalene rises from ~2 in HM to ~15 in the case of the catalyst of Example 4.

EXAMPLE 7

The conversion of methanol to gaseous and liquid hydrocarbin products was performed using the system and procedure as described in Example 2. Results for the catalysts of Examples 5 and 6 are given in Table 3. The catalysts are effective in production of an aromatic-rich gasoline-like hydrocarbon mixture and of a gaseous product rich in olefins.

TABLE 1

| | Zeolite catalyzed naphthalene methylation | | |
|---|---|---|---|
| Catalyst | Ex. 1[a] | HM[b] | HY[c] |
| Catalyst weight, g | 0.5 | 5 | 5 |
| WHSV, $h^{-1}$ | 3.16 | 1.18 | 1.18 |
| Temperature, °C. | 400 | 400 | 450 |
| Time on stream, h | 0.5 | 0.5 | 1.3 |
| Conversion, % | 5 | 29 | 47 |
| Product analysis, d wt % | | | |
| MN | 50.2 | 55.5 | 44.1 |
| EN | 10.4 | 4.4 | 1.1 |
| DMN | 33.1 | 26.1 | 28.7 |
| TMN | 5.6 | 10.5 | 18.7 |
| TEMN | 0.7 | 2.7 | 6.3 |
| PMN | — | 0.6 | 1.1 |
| MN isomer composition, % | | | |
| Beta | 89 | 65 | 63 |
| Alpha | 11 | 35 | 37 |
| DMN isomer composition, % | | | |
| 2,6 + 2,7 | 65.6 | 35.1 | 32.2 |
| 1,3 | 14.0 | 29.6 | 30.0 |
| 1,6 | 12.9 | 17.9 | 18.2 |
| 2,3 + 1,4 + 1,5 | 5.4 | 11.5 | 13.3 |
| 1,2 | 2.1 | 5.9 | 6.3 |
| 1,8 | 0.0 | 0.0 | 0.0 |

[a]Catalyst obtained in Example 1.
[b]H-Mordenite, see text.
[c]See text.
[d]MN = methylnaphthalene, EN = ethyinaphthalene, DMN = dimethylnaphthalene, TMN = trimethylnaphthalene, TEMN = tetramethylnaphthalene, PMN = pentamethylnaphthalene.

TABLE 2

| Catalyst | HM | | Ex. 3 | | Ex. 4 | | | Ex. 5 | | Ex. 6 | |
|---|---|---|---|---|---|---|---|---|---|---|---|
| Catalyst weight, g | 5 | | 0.5 | | 0.5 | | | 0.5 | | 0.5 | |
| Feed, g: | | | | | | | | | | | |
| MeOH | 3.8 | | 2.0 | | 2.0 | 2.0 | 0.5 | 2.0 | | 2.0 | |
| Mesitylene | 7.7 | | 7.0 | | 6.0 | 6.0 | 6.0 | 6.0 | | 6.0 | |
| Naphthalene | 2.3 | | 2.0 | | 2.0 | 2.0 | 2.0 | 2.0 | | 2.0 | |
| Flow, ml/h | 5.0 | | 3.8 | | 3.9 | 2.1 | 4.2 | 4.0 | | 4.2 | 2.05 |
| Time on stream, h | 2 | 4 | 2 | 3 | 2 | 4 | 2 | 2 | 1 | | 3 |
| Analysis: | | | | | | | | | | | |
| MeOH | 0.3 | 0.55 | 0.72 | 0.67 | 1.1 | 0.76 | 0.27 | 1.3 | 0.73 | | 0.5 |
| C9 | 1.8 | 0.16 | 1.1 | 1.1 | 1.28 | 1.14 | 0.56 | 1.9 | 1.34 | | 1.0 |
| Mesitylene | 64.4 | 66.5 | 69.8 | 69.8 | 65.1 | 64.5 | 54.6 | 49.6 | 52.3 | | 50.7 |
| TEMB | 7.8 | 1.1 | 6.9 | 2.4 | 1.0 | 0.76 | 1.5 | — | — | | — |
| PMB | 3.4 | 7.1 | 2.4 | 0.95 | 0.7 | 0.78 | 0.6 | 0.1 | 0.09 | | 0.14 |
| Naphthalene | 18.6 | 20.0 | 24.9 | 23.26 | 28.6 | 30.2 | 40.1 | 46.5 | 44.7 | | 47.0 |
| Beta-MN(2-MN) | 1.01 | 1.25 | 1.08 | 0.94 | 1.28 | 1.11 | 1.63 | 0.23 | 0.33 | | 0.29 |
| Alpha-MN(1-MN) | 0.95 | 1.12 | 0.18 | 0.15 | 0.09 | 0.1 | 0.12 | 0.01 | 0.013 | | 0.008 |
| 2,6 + 2,7-DMN | 0.18 | 0.33 | 0.44 | 0.35 | 0.31 | 0.29 | 0.32 | 0.07 | 0.07 | | 0.05 |
| 1,3 + 1,6-DMN | 0.21 | 0.20 | 0.17 | 0.11 | 0.14 | 0.12 | 0.12 | 0.03 | 0.04 | | 0.01 |
| higher prod. | 0.22 | 0.21 | 0.046 | 0.02 | 0.11 | 0.05 | 0.05 | — | — | | — |
| %2-MN -MN in total MN | 52 | 53 | 86 | 86 | 93.5 | 92 | 93.2 | 96 | 96 | | 97 |
| %2-MN -MN in total prod. | 39 | 40.2 | 64 | 60 | 66.3 | 66.5 | 73 | 68 | 73 | | 80.4 |
| Conversion, % | 10.5 | 13.5 | 7.2 | 6.4 | 6.3 | 5.2 | 5.3 | 0.7 | 1.0 | | 0.75 |

TABLE 3

| Catalyst | Ex. 5 | | Ex. 6 | |
|---|---|---|---|---|
| Catalyst weight, g | 1 | | 1 | |
| Temperature, °C. | 370 | | 370 | |
| Feed flow, ml/h (Meoh) | | 5.1 | | |
| Time on stream, h | 1 | 2 | 1 | 4 |
| Conversion, % | 100 | 100 | 100 | 100 |
| Product analysis | | | | |
| 1. gas, % (without carrier gas) | | | | |
| carbon dioxide | 0.01 | 0.01 | 0.003 | |
| ethene | 1.80 | 1.8 | 2.78 | |
| ethane | 0.08 | 0.8 | — | |
| water | 0.04 | — | — | |
| propane | 2.45 | 4.70 | 4.19 | |
| propane | 1.73 | 1.78 | 1.77 | |
| dimethyl ether | 0.25 | 1.16 | 0.4 | |
| C4+ | — | 2.55 | 5.29 | |
| 2. Liquid, % | | | | |
| C6+ methanol | 24.0 | 16.3 | 26.1 | 14.2 |
| benzene | 0.45 | 0.49 | — | — |
| toluene | 11.9 | 9.8 | 11.0 | 6.4 |

TABLE 3-continued

| | | | | |
|---|---|---|---|---|
| ethylbenzene | 1.35 | 1.7 | 0.46 | 1.6 |
| p-xylene | 25.6 | 24.7 | 32.4 | 30.5 |
| m-xylene | 21.2 | 25.2 | 15.1 | 15.6 |
| o-xylene | 7.8 | 4.1 | 4.0 | 5.3 |
| p-ethyltoluene | 3.7 | 4.8 | 3.4 | 6.4 |
| m-ethyltoluene | 3.2 | 3.6 | 3.0 | 5.2 |
| o-ethyltoluene | 0.4 | — | — | — |
| pseudocumene | 0.4 | 8.6 | 4.4 | 13.2 |
| other C$_9$+ aromomatics | — | 0.58 | — | 0.8 |

We claim:

1. A method of preferred beta-position alkylation of a substrate comprising naphthalene or a derivative thereof, which comprises reacting the substrate with a C$_1$–C$_3$-alkanol or C$_2$–C$_3$-olefin alkylating agent while contacting the substrate and alkylating agent with a catalyst selected from the group consisting of a crystallized borosilicate glass zeolite alkylation catalyst and a crystalline silica-alumina catalyst at 400°–500°, said catalyst being at least 86% beta selective with respect to the alkylation of naphthalene by said alkylating agent at 400°–500° C.

2. The method of claim 1, wherein said crystallized borosilicate glass zeolite has been crystallized from a reaction system comprising a source of finely powdered borosilicate glass and a template for a reaction time of less than 24 hours.

3. The method of claim 2, wherein the template is a tetraalkylammonium hydroxide, chloride, iodide, or bromide.

4. The method of claim 3, wherein the template is tetraalkylammonium hydroxide.

5. A method according to claim 1, wherein said catalyst is a ZSM-5 catalyst.

6. A method according to claim 1, wherein the alkylating agent is a C$_1$–C$_3$ alkanol.

7. The process of claim 1, wherein said catalytic conversion occurs in the presence of mesitylene.

* * * * *